United States Patent [19]

Hinshaw et al.

[11] 4,170,986

[45] Oct. 16, 1979

[54] POSTURAL DRAINAGE DEVICE

[75] Inventors: Cecil E. Hinshaw, Boulder, Colo.; Pauline S. Hinshaw, 35 S. 35th St., Boulder, Colo. 80303

[73] Assignee: Pauline S. Hinshaw, Boulder, Colo.

[21] Appl. No.: 939,440

[22] Filed: Sep. 5, 1978

[51] Int. Cl.$^2$ .............................................. A61B 19/00

[52] U.S. Cl. ..................................... 128/1 R; 211/198

[58] Field of Search ..................... 128/1 R, 68, 75, 69; 182/153, 144, 141; 211/198; 248/166; 297/423; 5/338; 272/144, 109, 93; 269/328, 327, 322

[56] References Cited

U.S. PATENT DOCUMENTS

| | | | |
|---|---|---|---|
| 2,245,661 | 6/1941 | Fievoh | 182/141 |
| 2,343,557 | 3/1944 | Johnson | 182/186 |
| 2,887,151 | 1/1958 | Springer | 128/680 X |
| 3,413,664 | 12/1968 | Dahlberg | 128/680 X |
| 3,490,558 | 1/1970 | Foley | 182/129 |
| 3,491,385 | 1/1970 | Werner | 5/327 |
| 3,493,225 | 2/1970 | Ceraldi | 182/131 |

FOREIGN PATENT DOCUMENTS

| | | | |
|---|---|---|---|
| 7947 | 6/1902 | Austria | 272/144 |
| 1291572 | 3/1962 | France | 269/328 |
| 353778 | 7/1931 | United Kingdom | 248/166 |

*Primary Examiner*—Robert W. Michell
*Assistant Examiner*—J. L. Kruter
*Attorney, Agent, or Firm*—Burton & Dorr

[57] ABSTRACT

A postural drainage device for supporting a patient comfortably in a position in which mucus and other matter can drain by gravity from his respiratory system. The invention includes a first embodiment which is portable and collapsible and assumes a substantially A-shape when in use. The two side members of the A-shape are pivotally mounted to each other adjacent the apex of the A-shape and provided with an adjustable knee support mounted on one of the side members, a pair of spaced-apart hand grips positioned adjacent the apex of the A-shape, and a pair of adjustable shoulder supports mounted in a spaced-apart relationship on the other side member with a hole cut through that side member into the interior of the A-shape providing access to a tray placed on the transverse member of the A-shape. The hand grips extend slightly above the apex of the A-shape to help maintain the patient therebetween on the apex. The patient's knees are supported on the knee support, his mid-section on the apex of the A-shape between the hand grips, and his shoulders on the spaced-apart shoulder supports with his head extending downwardly therebetween through the hole. In a second embodiment, leaf members corresponding to the two side members of the A-shaped embodiment are pivotally mounted to a main body and individually moved by respective piston-cylinder arrangements.

12 Claims, 9 Drawing Figures

POSTURAL DRAINAGE DEVICE

FIELD OF THE INVENTION

This invention relates to the field of postural drainage devices for supporting a patient comfortably in a position in which mucus and other matter can drain by gravity from his respiratory system.

BACKGROUND OF THE INVENTION AND PRIOR ART

Several diseases including staph pneumonia and cystic fibrosis require frequent positioning of the patient's body so that mucus and other matter can drain by gravity from his respiratory system. Such postural drainage is commonly accomplished by placing the patient prone on a hospital or other special bed with his head turned to one side and tipping the bed to lower his head. Most patients find this to be an extremely awkward position in which to cough and often times must be raised back up to a horizontal position before they can effectively cough. Further, the natural coughing position, especially in hard coughing, is with the body bent at the waist and not straight as in the bed tipping technique.

Another technique for postural drainage is disclosed in U.S. Pat. No. 3,413,664 to Dahlberg issued on Dec. 3, 1968. In this technique, the patient leans over the edge of a bed and places his upper torso on a downwardly inclined, main board with the top of his head against another board. A hole is provided in the main board through which the patient can expel mucus and other matter out of his mouth. This technique has numerous drawbacks. Notably, the patient's head is supported against a board 17 which can be very uncomfortable over the five to twenty minutes often needed for proper drainage and which would be totally unacceptable for patients with head, neck, or back problems. Further, Dahlberg's technique does not allow for head and neck movement and therefore, makes it more difficult for the patient to effectively cough, especially hard coughing, and to expel the mucus from his mouth, especially if he is trying to expel the mucus into a receptacle.

U.S. Pat. No. 3,491,385 to Werner issued on Jan. 27, 1970 discloses a postural drainage rest in his FIGS. 1, 2, and 4 in which the patient leans over an inclined surface to assume an inverted sitting position with his legs bent and with his mid-section, upper torso, arms, hands, and head supported on the rest. This inverted sitting position with legs bent that the patient assumes in this embodiment is difficult to hold over any length of time and it is fairly tiring. Further, the support 17 prevents effective movement of the head especially during hard coughing and the rest offers no support for the knees against which the patient could press for more effective coughing, especially during hard coughing. Werner discloses a second embodiment in his FIG. 3 to be used with a bed or table in which the patient kneels on the bed and leans over the rest supporting his mid-section and upper torso on the rest with his head extending over the edge 29 of the bed. This embodiment in use offers support for the knees, mid-section, and upper torso but none for the shoulders, arms, or hands. Also, movement of the head in this second embodiment is severely limited by the edge 29 thereby preventing effective hard coughing and requiring the patient to raise his head to expel the mucus into any receptacle located below the edge 29. From a practical standpoint, the embodiment of FIG. 3 is relatively unsafe since it positions the patient with his neck and Adam's apple at the horizontal edge between the upper and and side surfaces of the bed or table which can be very dangerous when the patient coughs.

U.S. Pat. No. 2,887,151 to Springer illustrates a proctological support in which the patient supports himself entirely on his knees and arms.

SUMMARY OF THE INVENTION

The present invention involves a postural drainage device for supporting a patient comfortably in a position in which mucus and other matter can drain by gravity from his respiratory system. In a first embodiment, the device is portable and collapsible and assumes a substantially A-shape when in use. The two side members of the A-shape are pivotably mounted to each other adjacent the apex of the A-shape and each side member has a first substantially planar surface facing interiorly of the A-shape and a second substantially planar surface facing exteriorly of the A-shape. A knee support is mounted on the exteriorly facing surface of one of the side members and a pair of spaced-apart hand grips are positioned adjacent the apex of the A-shape. On the exteriorly facing surface of the other side member, a pair of shoulder supports are mounted in a spaced-apart relationship and a hole is cut through the side member between the shoulder supports to the interior of the A-shape.

In use, the patient grips the hand grips, kneels on the knee support, pulls himself up to lean over the apex of the A-shape, extends his hands to the shoulder supports, and lowers himself until his shoulders are supported on the shoulder supports with his head extending downwardly therebetween through the hole. In the preferred embodiments, the hand grips extend above the apex of the A-shape to help maintain the patient's mid-section therebetween on the apex. The transverse member of the A-shape has a portion positioned beneath the patient's mouth and a tray can be placed on this portion to receive mucus and other matter expelled by the patient through his mouth. In the preferred manner of operation, the patient's knees are supported on the knee support, his mid-section on the apex of the A-shape, and his shoulders on the spaced-apart shoulder supports with his head extending downwardly therebetween through the hole. In this manner, the patient's arms and hands are free to perform other tasks and his head and neck are free to move for more effective coughing and expulsion of mucus through his mouth. With his hands free, the patient can selectively position them between various parts of his upper torso and the exteriorly facing surface of the side member for better drainage, grip various parts of the device to adjust his position thereon for better drainage and comfort, or hold a misting mask to his nose and mouth while he is on the drainage device. The knee support and shoulder supports are adjustably and removably mounted on the respective side members and can be selectively positioned to accommodate a particular patient's body dimensions.

The A-shaped embodiment is collapsible and in the collapsed position, the side members are moved about the pivotal axis until the two interiorly facing surfaces are substantially flush. The transverse member of the A-shape is movably mounted to one or both of the side members and is moved to a position between the two interiorly facing surfaces when the postural drainage device is in its collapsed position. In one embodiment, the transverse member is one-piece and is pivotally mounted to only one side member for movement between a transverse position forming the A-shape with the side members and a position extending along the one side member. In another embodiment, the transverse member is formed of two pieces. Each of the pieces is pivotally mounted to one of the two side members and to each other. The transverse member of the embodiment can be moved between a first position in which the two pieces are substantially co-planar forming the A-shape with the side members and a second position in which the transverse member forms a substantially inverted V-shape with each of the two pieces thereof extending respectively along one of the side members when the drainage device is in its collapsed position.

In a second embodiment, leaf members corresponding to the two side members of the A-shaped embodiment are pivotally mounted to a main body and individually moved by respective piston-cylinder arrangements to various positions relative to each other. The leaf members of this second embodiment have substantially planar surfaces which can be moved by the piston-cylinder arrangements to numerous positions including a substantially co-planar position and a substantially inverted V-shaped position. With the second embodiment, the leaf members can be moved to their substantially co-planar position and a patient placed thereon facing downwardly. The leaf members can then be selectively lowered to form the substantially inverted V-shape with the patient assuming a comfortable position for drainage in which his knees are supported on the knee support, his mid-section on the apex of the inverted V-shape, and his shoulders on the spaced-apart shoulder supports with his head extending downwardly therebetween. Alternately, the leaf members of this second embodiment can be positioned in any desired inverted V-shape and the patient can mount it and assume the drainage position in a manner similar to the A-shaped embodiment. As in the A-shaped embodiment, the knee support and shoulder supports of the second embodiment are adjustably and removably mounted on the respective leaf members and can be selectively positioned to accommodate a particular person's body dimensions.

OBJECTS OF THE INVENTION

It is an object of this invention to provide a new and novel postural drainage device on which a patient can assume a comfortable position for drainage.

It is an object of this invention to provide a new and novel postural drainage device on which the patient is supported with his arms and hands free to perform other tasks and his head and neck free to move for more effective coughing and expulsion of mucus and other matter through his mouth.

Another object is to provide a new and novel postural drainage device which is portable and collapsible and can provide a convenient support for a receptacle into which the patient can expel the mucus and other matter.

Another object is to provide a new and novel postural drainage device that is adjustable.

It is an object to provide a new and novel postural drainage device that supports the patient's knees, mid-section, and shoulders leaving his arms and hands free to perform other tasks.

It is an object to provide a new and novel postural drainage device in which the patient's shoulders are supported on spaced-apart supports leaving his arms and hands free to perform other tasks and his head and neck free to move for more effective coughing and expulsion of mucus and other other matter through his mouth.

It is an object to provide a new and novel postural drainage device which can be easily mounted and dismounted by most patients without assistance so that the device can be used at home.

Another object is to provide a new and novel postural drainage device with adjustable leaf members so that a critically ill or weak patient can be placed on the device and the leaf members moved to a substantially inverted V-shape for effective drainage without the patient having to exert any effort.

Another object is to provide a new and novel postural drainage device which can form a substantially inverted V-shape and has hand grips extending above the apex of the V-shape to help maintain the patient's mid-section therebetween on the apex.

It is an object to provide a new and novel postural drainage device on which the patient can assume any number of different positions for effective drainage.

It is an object to provide a new and novel support on which the patient can assume a comfortable position for a proctological or other exam.

Additional objects as well as features and advantages of this invention will become evident from the descriptions set forth hereinafter when considered in conjunction with the accompanying drawings.

BRIEF DESCRIPTION OF THE DRAWINGS

FIG. 3 also shows the position of the hole for the head that extends through the side member between the shoulder supports. Another feature in FIG. 3 is the hand grips which are spaced-apart and extend above the apex of the A-shape to help maintain the patient's mid-section therebetween on the apex.

FIG. 4 also illustrates the hand grips which are spaced-apart and extend above the apex of the A-shape to help maintain the patient's mid-section therebetween on the apex.

FIG. 8 illustrates the relative locations of the knee support, hand grips, upper torso support, spaced-apart shoulder supports, hole for the head, and additional hand grips adjacent the shoulder supports. FIG. 8 also illustrates that most of these members are adjustably mounted to the respective side members so that they can be moved to accommodate a particular patient's body dimensions.

DETAILED DESCRIPTION OF THE PREFERRED EMBODIMENTS

Figure 1:
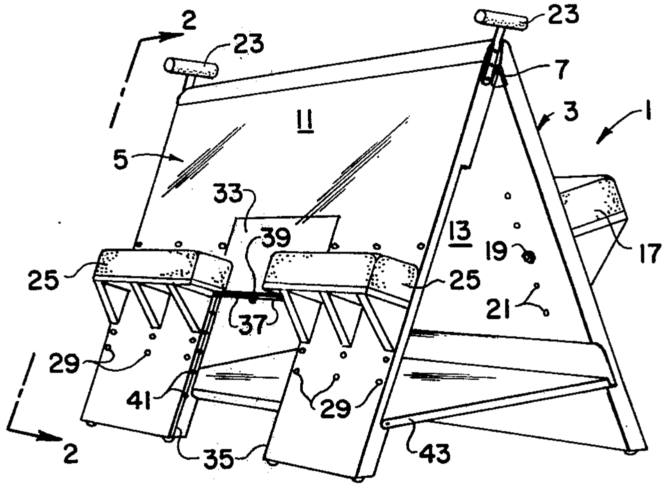
FIG. 1 is a perspective view of a first embodiment of the invention in which the postural drainage device is portable and collapsable and assumes a substantially A-shape when in use.
Figure 2:
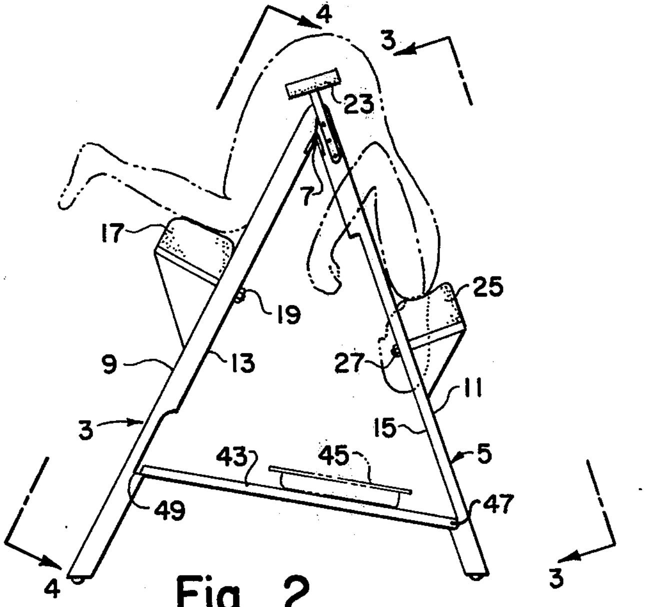
FIG. 2 is a side view along line 2—2 of FIG. 1 illustrating a preferred position the patient can assume on the device. In this preferred position, his knees are supported on the knee support, his mid-section on the apex of the A-shape between the hand grips, and his shoulders on the spaced-apart shoulder supports with his arms and hands free to perform other tasks and his head and neck free to move for more effective coughing and expulsion of mucus and other matter through his mouth.
Figure 3:
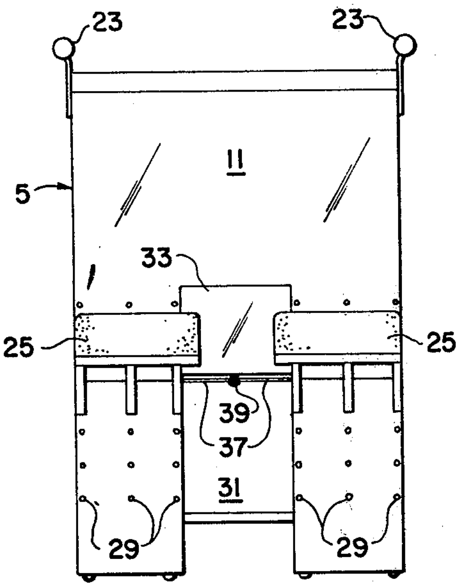
FIG. 3 is a view along line 3—3 of FIG. 2 showing the spaced-apart relationship of the shoulder supports on one side member of the A-shape.
Figure 4:
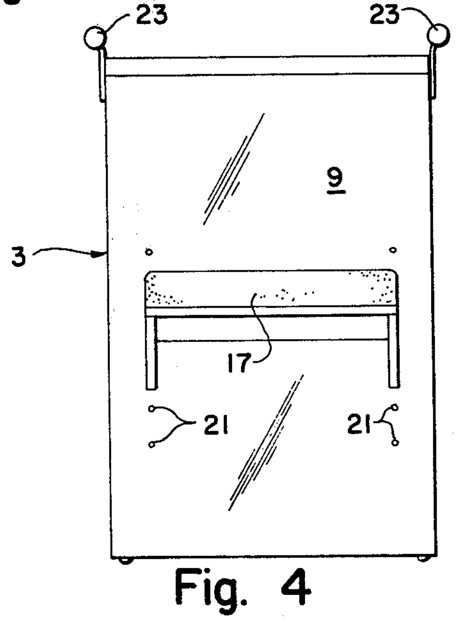
FIG. 4 is a view along line 4—4 of FIG. 2 showing the other side member of the A-shape on which the knee support is mounted.
Figure 5:
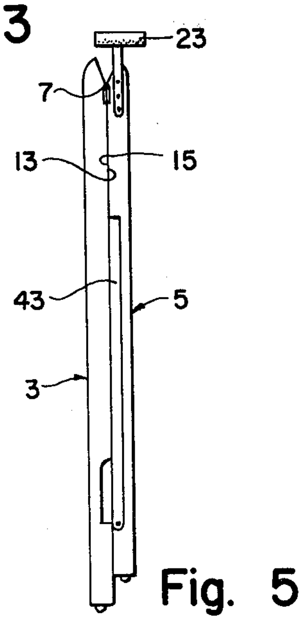
FIG. 5 is a side view similar to that of FIG. 2 illustrating the postural drainage device of FIGS. 1–3 in its collapsed position in which the transverse member extends along the interiorly facing planar surface of one of the side members and the side members are substantially flush and parallel to each other.

FIGS. 1–6 illustrate a first embodiment of the invention in which the postural drainage device 1 is portable and collapsible and assumes a substantially A-shape when in use. The device 1 has two side members 3 and 5 which are pivotally mounted to each other at 7 adjacent the apex of the A-shape. Each side member 3 and 5 has a substantially planar surface 9 and 11 respectively facing exteriorly of the A-shape and a substantially planar surface 13 and 15 respectively facing interiorly of the A-shape. A knee support 17 is adjustably and removably mounted to the side member 3 adjacent the surface 9 thereof by bolts 19 which can be selectively received in holes 21 and support 17 as desired. A pair of hand grips 23 are mounted adjacent the apex of the A-shape and can be griped by the patient to help him mount and dismount the device 1. As shown in FIGS. 1, 3, and 4, each hand grip 23 is mounted respectively adjacent one of the end portions of the apex. In the preferred embodiment, a portion of each hand grip 23 extends above the apex of the A-shape to help maintain the patient's mid-section between the hand grips 23 on the apex.

A pair of shoulder supports 25 are adjustably and removably mounted to the side member 5 adjacent the surface 11 thereof by bolts 27 as shown in FIGS. 1–3. The bolts 27 can be selectively received in holes 29 and the respective shoulder supports 25 as desired whereby the shoulder supports 25 can be selectively moved toward and away from each other and the pivotal axis 7. In the preferred manner, the shoulder supports 25 are mounted in a spaced-apart relationship so that the patient's shoulders can be supported thereon with his arms and hands free to perform other tasks and his head extending downwardly therebetween through the hole 31. Side member 5 also has an adjustable support member 33 for the upper chest of the patient as illustrated in FIGS. 1 and 3. This support member 33 is received on the runners 35 and can be selectively moved toward and away from the apex of the A-shape by withdrawing the arms 37 of the toggle arrangement 39, sliding the support member 33 on the runners 35 to a new location, and extending the arms 37 back outwardly into a different pair of receiving holes 41.

Figure 6:
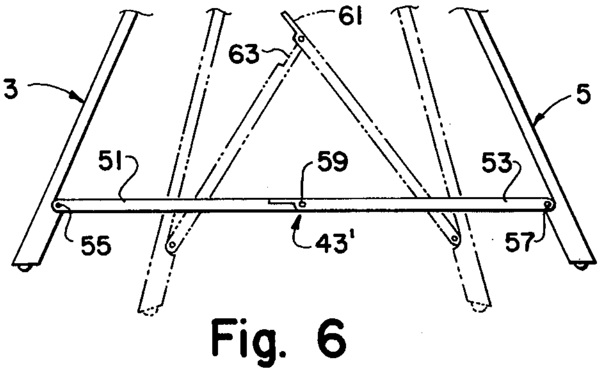
FIG. 6 illustrates a second manner in which the transverse member of the A-shape can be constructed. In this modification, the transverse member has two pieces which are pivotally mounted to each other and to one of the respective side members of the A-shape. The transverse member assumes a substantially planar position when the device is in use and a substantially invert V-shape when the device is in its collapsed position.

The postural drainage device 1 of the first embodiment has a transverse member 43 extending substantially between the side members 3 and 5 to form the A-shape. In the preferred manner of operation, a pan 45 is placed on a portion of the transverse member 43 to receive mucus and other matter expelled from the patient's mouth. As illustrated in FIG. 2, the portion of the transverse member on which the pan 45 is supported is at a location adjacent to and lower than the portion of the hole 31 at which the patient's mouth is located when he is supported on the device 1. Transverse member 43 is pivotably mounted at 47 to the side member 5 and can be moved from the position shown in FIG. 2 in which one edge of the transverse member 43 is supported on the support 49 to the collapsed position shown in FIG. 5. In the collapsed position of FIG. 5, the transverse member 43 extends substantially along a portion of side member 5 and the interiorly facing surfaces 13 and 15 are substantially parallel and flush with each other. In the modification of FIG. 6, the transverse member 43' is formed of two pieces 51 and 53. Each of the pieces 51 and 53 is pivotably mounted to one of the two side members 3 and 5 at 55 and 57 and to each other at 59. The transverse member 43' can be moved between a first position in which detent 61 is received in groove 63 and the two pieces 51 and 53 are substantially co-planar forming the A-shape with the side members 3 and 5 and a second position in which it forms a substantially inverted V-shape with each of the two pieces 51 and 53 extends respectively along one of the side members 3 and 5 when the drainage device 1 is in its collapsed position.

In operation, the patient grips the hand grips 23, kneels on the knee support 17, pulls himself up to lean over the apex of the A-shape, extends his hands to the shoulder supports 25, and lowers himself until his shoulders are supported on the shoulder supports 25 with his head extending downwardly therebetween through the hole 31. The hand grips 23 extend above the apex of the A-shape to help maintain the patient's mid-section therebetween on the apex. The transverse member 43 or 43' of the A-shape has a portion positioned beneath the patient's mouth and a tray 45 can be placed on this portion to receive mucus and other matter expelled by the patient through his mouth. In the preferred manner of operation, the patient's knees are supported on the knee support 17, his mid-section on the apex of the A-shape, and his shoulders on the spaced-apart shoulder supports 25 with his head extending downwardly therebetween through the hole 31. This enables the patient's arms and hands to remain free to perform other tasks and his head and neck free to move for more effective coughing and expulsion of mucus through his mouth. The knee support 17 and shoulder support 25 are adjustably and removably mounted on the respective side members 3 and 5 and can be selectively positioned to accommodate a particular patient's body dimensions including shoulder separation and mid-section to shoulder length. Support member 33 can also be selectively adjusted toward and away from the apex of the A-shape to give more comfort to the patient. With the device 1, the patient's hands are free and can be selectively positioned between various parts of his upper torso and the exteriorly facing surface 11 of the side member 5 for better drainage and comfort. He can also grip various parts of the device 1 with his hands to adjust his position thereon for better drainage and comfort and can hold a misting mask to his nose and mouth while he is on the drainage device 1 if needed. In this manner, the patient can combine the steps of drainage and misting while on the device 1.

Figure 7:
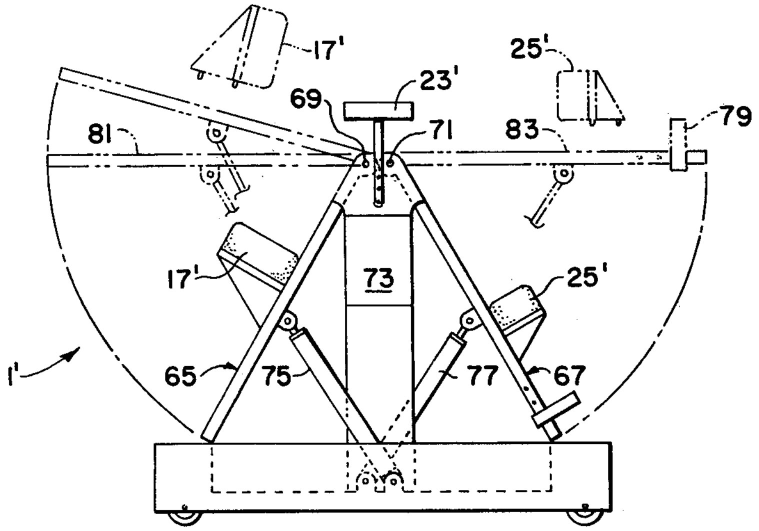
FIG. 7 illustrates a second embodiment of the invention in which leaf members corresponding to side members of the A-shaped embodiment are pivotally mounted to a main body for movement between a variety of positions including one in which the leaf members are substantially co-planar and a second position in which they assume a substantially inverted V-shape. In this second embodiment, a critically ill or weak patient can be placed on the leaf members when they are in their substantially co-planar position and then the leaf members can be lowered to a substantially inverted V-shape so that the patient is in a comfortable position for effective coughing and expulsion of mucus and other matter through his mouth.
Figure 8:
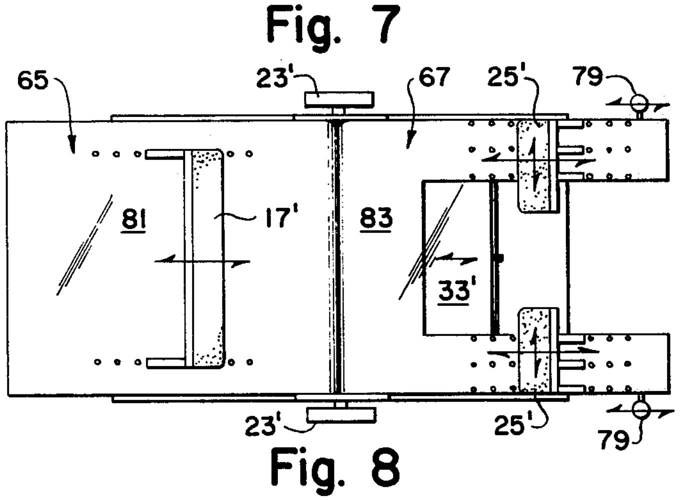
FIG. 8 is a top view of the embodiment of FIG. 7 with the leaf members in their substantially co-planar position.

In the second embodiment 1' of FIGS. 7–8, leaf members 65 and 67 corresponding to the side members 3 and 5 of the A-shaped embodiment are pivotally mounted respectively at 69 and 71 to the main body 73. The leaf member 65 and 67 can be individually moved by the respective piston-cylinder arrangements 75 and 77 to various positions relative to each other. As in the first embodiment, the second embodiment of FIGS. 7–8 has a knee support 17' and a pair of shoulder supports 25' which are adjustably and removably mounted to the respective leaf members 65 and 67. The second embodiment also includes a first pair of hand grips 23' and further includes a second pair of hand grips 79 that can be selectively mounted above, below, or even with the shoulder supports 25' in whatever location is most helpful to the patient in mounting and dismounting the device 1'. The second embodiment 1' also has a support member 33' which can be selectively moved toward and away from the pivotal axis 71 of the leaf member 67 to more comfortably support the upper chest of the patient thereon.

In one preferred manner of operation of the second embodiment 1', the leaf members 65 and 67 are moved so that their substantially planar surfaces 81 and 83 are substantially co-planar. A critically ill or weak patient can then be placed on the surfaces 81 and 83 facing downwardly and the leaf members 65 and 67 selectively lower to form a substantially V-shape. In this manner, the patient assumes a comfortable position for drainage on the device 1' in which his knees are supported on the knee support 17', his mid-section on the apex of the inverted V-shape, and his shoulders on the spaced-apart shoulders supports 25' with his head extending downwardly therebetween through the hole. Alternately, the leaf members 65 and 67 of the second embodiment 1' can be positioned in any desired inverted V-shape and the patient can mount it and assume the drainage position in a manner similar to the A-shaped embodiment. In both of these modes of operation, the patient's arms and hands are free to move as is his neck and head. If desired, the leaf member 65 can be mounted so that it can be moved above a substantially horizontal position as shown in dotted lines in FIG. 7 and the knee support 17' removed so that the patient assumes a substantially inverted position with his feet in the air and his body extending downwardly with his shoulders supported on the spaced-apart shoulder supports 25'.

Figure 9:
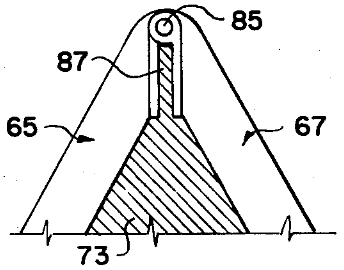
FIG. 9 is an enlarged side view of a modified pivot arrangement for the leaf members in which the leaf members have a common pivotal axis.

FIG. 9 illustrates a modification of the pivot arrangement of leaf members 65 and 67 in which the leaf members are mounted for pivotal movement about a common axis 85. In this modification, the main body 73 has an upwardly extending portion 87 which has knuckles extending along the knuckles of leaf members 65 and 69 to receive the pivot pin 85.

While two embodiments of the present invention have been described in detail herein, various changes and modifications may be made without departing from the scope of the invention. For example, it is contemplated that padding can be added to both of the embodiments of the present invention wherever desired to increase the patient's comfort so that he can remain on the devices 1 and 1' as long as possible. It is also contemplated that differently shaped padding or pillows can be used to further increase the efficiency of the patient's drainage. For example, a wedge shaped pillow could be placed under one of the lungs to raise that side of the patient's body and tilt it toward the patient's middle so that mucus and other matter can drain more easily therefrom. It is also contemplated that the size of the devices 1 and 1' could be increased or decreased to accommodate differently sized patients as for example, a children's model of each embodiment could be made and that the device could be used for proctological or other exams. It is further contemplated that straps or other restraints could be used to help secure the patient on the devices 1 and 1'. The knee supports 17 and 17' and shoulder supports 25 and 25' as well as hand grips 79 are shown to be mechanically adjustable on the devices 1 and 1' and it is contemplated that they could be moved by a gear or ratchet arrangement operated by hand cranks or even hydraulically or electrically moved so they could be adjusted while the patient was on the device 1 and 1'. The controls for the piston-cylinder arrangements 75 and 77 have not been shown; however, it is anticipated that one set of controls could be positioned for easy access by an attendant and another set of controls could be conveniently positioned near the shoulder supports 25 and 25' for easy access by the patient while he was on the postural drainage device 1 or 1'. The first embodiment of FIGS. 1–6 is shown as assuming a non-adjustable A-shaped position when in use with the abutting surfaces of side members 3 and 5 above the pivotal axis 7 defining the maximum separation of the side members 3 and 5. If desired, this embodiment can be made adjustable as for example by providing turnbuckles between the side members 3 and 5 with one end of each turnbuckle permanently attached to one side member and the other end removably attached to the other side member so the device 1 can still be collapsed. The transverse member could then be designed to telescope or a series of parallel grooves could be cut in each side member and the transverse member selectively positioned therein depending upon what angle the side members 3 and 5 assume. In both embodiments and in all positions assumed by the patient, percussion by a therapist is more effective with the patient facing downwardly. In this manner, the patient can easily cought at any time and the percussion is done with the patient's chest against a hard, padded surface.

We claim:

1. A postural drainage device for supporting a patient comfortably in a position in which mucus and other matter can drain by gravity from his respiratory system, said device comprising:

a main body, first and second members, and means for pivotally mounting each of said first and second members to said body for movement about a substantially horizontal axis, each of said first and second members having a substantially planar surface and being mounted to said main body with the respective surfaces facing upwardly, means for selectively moving each of said first and second members about the respective pivotal axis at least between a first position in which said surfaces are substantially co-planar and a second position in which said surfaces form a substantially inverted V-shape, a pair of shoulder supports and means for mounting said pair of shoulder supports to said first member adjacent said surface thereof in a spaced-apart relationship, at least one knee support and means for mounting said knee support to said second member adjacent the surface thereof whereby in one mode of operation, said substantially planar surfaces can be moved by said moving means to said first, substantially co-planar position, the patient placed thereon facing downwardly, and said surfaces moved by said moving means to said second, substantially inverted V-shaped position with the patient assuming a comfortable position for drainage in which his knees are supported on the knee support, his mid-section on the apex of said inverted V-shape, and his shoulders on said spaced-apart shoulder supports with his head extending downwardly therebetween and whereby in a second mode of operation, the surfaces can be moved by said moving means to said second, substantially inverted V-shaped position and the patient can assume said comfortable position for drainage by kneeling on said knee support and leaning over said surfaces with his mid-section supported on the apex of said inverted V-shape and his shoulders supported on said spaced-apart shoulder supports with his head extending downwardly therebetween, and a pair of hand grips and means for mounting said hand grips adjacent the apex of the inverted V-shape in a spaced-apart relationship, said apex having two end portions and each hand grip being mounted respectively adjacent one of said end portions whereby the patient can grip said pair of hand grips to assist himself onto and off of said knee support, apex of said inverted V-shape, and shoulder supports.

2. The postural drainage device of claim 1 further including an upper chest support member and means for mounting said upper chest support member for selective movement toward and away from the apex of the inverted V-shape substantially between said spaced-apart shoulder supports.

3. A postural drainage device for supporting a patient comfortably in a position in which mucus and other matter can drain by gravity from his respiratory system, said device comprising:

a main body, first and second members, and means for pivotally mounting each of said first and second members to said main body for movement about a substantially horizontal axis, each of said first and second members having a substantially planar surface and being mounted to said main body with the respective surfaces facing upwardly, means for selectively moving each of said first and second members about the respective pivotal axis at least between a first position in which said surfaces are substantially co-planar and a second position in which said surfaces form a substantially inverted V-shape, a pair of shoulder supports and means for mounting said pair of shoulder supports to said first member adjacent said surface thereof in a spaced-apart relationship, at least one knee support and means for mounting said knee support to said second member adjacent the surface thereof whereby in one mode of operation, said substantially planar surfaces can be moved by said moving means to said first, substantially co-planar position, the patient placed thereon facing downwardly, and said surfaces moved by said moving means to said second, substantially inverted V-shaped position with the patient assuming a comfortable position for drainage in which his knees are supported on the knee support, his mid-section on the apex of said inverted V-shape, and his shoulders on said spaced-apart shoulder supports with his head extending downwardly therebetween and whereby in a second mode of operation, the surfaces can be moved by said moving means to said second, substantially inverted V-shaped position and the patient can assume said comfortable position for drainage by kneeling on said knee support and leaning over said surfaces with his mid-section supported on the apex of said inverted V-shape and his shoulders supported on said spaced-apart shoulder supports with his head extending downwardly therebetween and, a pair of hand grips and means for mounting said hand grips adjacent the apex of the inverted V-shape in a spaced-apart relationship, said apex having two end portions and each hand grip being mounted respectively adjacent one of said end portions whereby the patient can grip said pair of hand grips to assist himself onto and off of said knee support, apex of said inverted V-shape, and shoulder supports, said mounting means for said hand grips mounting each of said hand grips with a portion thereof extending above the apex of said inverted V-shape to help maintain the patient's mid-section therebetween on said apex.

4. A substantially A-shaped postural drainage device for supporting a patient comfortably in a position in which mucus and other matter can drain by gravity from his respiratory system and for supporting a receptacle into which the patient can expel the mucus through his mouth, said device comprising:

at least two side members and means for pivotally mounting said side members to each other adjacent the apex of said A-shape for movement between an open position in which said side members form an acute angle and a collapsed position in which said side members are substantially flush with each other, at least one of said side members having a hole therethrough with a portion of said hole extending in a direction away from the apex of said A-shape to a first location on said one side member, and means for pivotally mounting said transverse member to at least one of said side members for movement between a first position extending substantially between said side members to form said substantially A-shape with a portion of said transverse member positioned at a second location adjacent to and lower than said first location and a second position extending substantially along a portion of said one side member when said side members are in said collapsed position whereby the receptacle can be placed on said portion of the transverse member when the transverse member is in said first position and the patient can lean over said A-shaped device with his mid-section supported on the apex of said A-shape and his mouth at said first location of said one side member and expel mucus into the receptacle on said transverse member.

5. The postural drainage device of claim 4 further including an upper chest support member and means for mounting said upper chest support member to one of said side members for selective movement toward and away from the apex of the A-shape.

6. A postural drainage device for supporting a patient comfortably in a position in which mucus and other matter can drain by gravity from his respiratory system, said device comprising:

a first portion having a surface, means for supporting said first portion with said surface at an inclined angle to a horizontal plane and facing upwardly, a pair of shoulder supports, and means for mounting said pair of shoulder supports to said first portion adjacent said surface in a spaced-apart relationship, a second portion having a surface and means for supporting said second portion adjacent said first portion with said surface of said second portion facing upwardly and forming a substantially inverted V-shape with the surface of said first portion, a knee support and means for mounting said knee support to said second portion adjacent the surface thereof whereby the patient can kneel on said knee support, lean over said surfaces with his mid-section supported on the apex of said inverted V-shape, extend his upper torso downwardly on the surface of said first portion, and rest his shoulders on the spaced-apart shoulder supports with his head extending downwardly therebetween, and, a pair of hand grips and means for mounting said pair of hand grips adjacent the apex of the inverted V-shape in a spaced-apart relationship, said apex having two end portions and each hand grip being mounted respectively adjacent one of said end portions whereby the patient can grip said pair of hand grips to assist himself onto and off of said knee support, apex of the inverted V-shape, and shoulder supports.

7. The postural drainage device of claim 6 wherein said mounting means for said hand grips mounts each of said hand grips with a portion thereof extending above the apex of said inverted V-shape to help maintain the patient's mid-section therebetween on said apex.

8. The postural drainage device of claim 6 wherein said first portion has a hole therethrough adjacent said shoulder supports and extending therebelow whereby the patient can expel said mucus and other matter through said hole when the patient is in said comfortable position.

9. The postural drainage device of claim 6 wherein said mounting means for said pair of shoulder supports includes means for selectively mounting each of said shoulder supports in any one of a number of locations on said surface whereby said shoulder supports can be positioned relative to each other and relative to said surface to suit a particular patient's body dimensions including shoulder separation and mid-section to shoulder length.

10. The postural drainage device of claim 6 wherein said supporting means for said first portion includes means for varying the size of said inclined angle.

11. The postural drainage device of claim 10 wherein said supporting means for said first portion includes a main body and means for pivotally mounting said first portion to said main body for movement about a substantially horizontal axis, said varying means including at least one fluid piston-cylinder member mounted between said main body and said first portion whereby fluid can be selectively supplied and withdrawn from said piston-cylinder member to expand and contract the piston-cylinder member and vary the inclined angle of said first portion.

12. The postural drainage device of claim 6 further including an upper chest support member and means for mounting said upper chest support member for selective movement substantially between said spaced-apart shoulder supports.

* * * * *